(12) United States Patent
Hashimoto et al.

(10) Patent No.: US 11,103,322 B2
(45) Date of Patent: Aug. 31, 2021

(54) REMOTE CONTROL ROBOT SYSTEM

(71) Applicant: KAWASAKI JUKOGYO KABUSHIKI KAISHA, Kobe (JP)

(72) Inventors: Yasuhiko Hashimoto, Kobe (JP); Masayuki Kamon, Akashi (JP)

(73) Assignee: KAWASAKI JUKOGYO KABUSHIKI KAISHA, Kobe (JP)

( * ) Notice: Subject to any disclaimer, the term of this patent is extended or adjusted under 35 U.S.C. 154(b) by 376 days.

(21) Appl. No.: 15/755,104

(22) PCT Filed: May 27, 2016

(86) PCT No.: PCT/JP2016/002594
§ 371 (c)(1),
(2) Date: Feb. 26, 2018

(87) PCT Pub. No.: WO2017/033365
PCT Pub. Date: Mar. 2, 2017

(65) Prior Publication Data
US 2018/0243922 A1 Aug. 30, 2018

(30) Foreign Application Priority Data
Aug. 25, 2015 (JP) .............................. JP2015-165479

(51) Int. Cl.
*B25J 9/00* (2006.01)
*A61B 34/37* (2016.01)
(Continued)

(52) U.S. Cl.
CPC .............. *A61B 34/37* (2016.02); *A61B 34/32* (2016.02); *B23P 19/04* (2013.01); *B23Q 15/12* (2013.01);
(Continued)

(58) Field of Classification Search
CPC .... A61B 34/37; A61B 34/32; G05B 19/4182; G06T 7/62; G06T 7/70; B25J 9/0081;
(Continued)

(56) References Cited

U.S. PATENT DOCUMENTS

2010/0224427 A1* 9/2010 Nuchter ................ B60B 19/125
180/7.1
2017/0144297 A1* 5/2017 Takaichi .................. B25J 19/00

FOREIGN PATENT DOCUMENTS

CN 101777250 A 7/2010
JP H09-216183 A 8/1997
(Continued)

OTHER PUBLICATIONS

JP2014-104527 in view of JPO English Translation (Year: 2014).*
(Continued)

*Primary Examiner* — Ian Jen
(74) *Attorney, Agent, or Firm* — Oliff PLC (57) ABSTRACT

Plurality of robot main bodies a remote control device including contactless action detecting part configured to detect contactless action including at least one given operation instructing action by operator, and control device communicably connected to remote control device and configured to control operations of plurality of robot main bodies, are provided. Control device includes memory part configured to store operational instruction content data defining operation mode of robot main body corresponding to the at least one operation instructing action, operational instruction content identifying module configured to identify operation mode of robot main body corresponding to one of operation instructing action detected by contactless action detecting part based on operational instruction content data, and motion controlling module configured to control operation of at least one given robot main body among plurality of
(Continued)

robot main bodies based on operation mode identified by operational instruction content identifying module.

4 Claims, 7 Drawing Sheets

(51) Int. Cl.
| | | |
|---|---|---|
| G05B 19/418 | (2006.01) | |
| B25J 9/16 | (2006.01) | |
| B23P 19/04 | (2006.01) | |
| B25J 13/00 | (2006.01) | |
| B25J 19/04 | (2006.01) | |
| B25J 13/08 | (2006.01) | |
| B25J 3/00 | (2006.01) | |
| B25J 13/06 | (2006.01) | |
| B25J 18/00 | (2006.01) | |
| B25J 19/02 | (2006.01) | |
| B25J 3/04 | (2006.01) | |
| B23Q 15/12 | (2006.01) | |
| B25J 13/02 | (2006.01) | |
| B25J 11/00 | (2006.01) | |
| G06F 3/01 | (2006.01) | |
| H04N 5/232 | (2006.01) | |
| H04N 7/18 | (2006.01) | |
| A61B 34/32 | (2016.01) | |
| G06T 7/62 | (2017.01) | |
| G06T 7/70 | (2017.01) | |
| B23P 21/00 | (2006.01) | |

(52) U.S. Cl.
CPC . *B25J 3/00* (2013.01); *B25J 3/04* (2013.01); *B25J 9/0081* (2013.01); *B25J 9/0084* (2013.01); *B25J 9/0087* (2013.01); *B25J 9/161* (2013.01); *B25J 9/1602* (2013.01); *B25J 9/163* (2013.01); *B25J 9/1612* (2013.01); *B25J 9/1628* (2013.01); *B25J 9/1633* (2013.01); *B25J 9/1638* (2013.01); *B25J 9/1641* (2013.01); *B25J 9/1646* (2013.01); *B25J 9/1653* (2013.01); *B25J 9/1664* (2013.01); *B25J 9/1669* (2013.01); *B25J 9/1674* (2013.01); *B25J 9/1682* (2013.01); *B25J 9/1689* (2013.01); *B25J 9/1697* (2013.01); *B25J 11/008* (2013.01); *B25J 13/00* (2013.01); *B25J 13/003* (2013.01); *B25J 13/006* (2013.01); *B25J 13/02* (2013.01); *B25J 13/025* (2013.01); *B25J 13/06* (2013.01); *B25J 13/065* (2013.01); *B25J 13/08* (2013.01); *B25J 13/084* (2013.01); *B25J 13/085* (2013.01); *B25J 13/087* (2013.01); *B25J 13/088* (2013.01); *B25J 18/00* (2013.01); *B25J 19/023* (2013.01); *B25J 19/028* (2013.01); *B25J 19/04* (2013.01); *G05B 19/4182* (2013.01); *G06F 3/017* (2013.01); *G06T 7/62* (2017.01); *G06T 7/70* (2017.01); *H04N 5/23219* (2013.01); *H04N 7/181* (2013.01); *B23P 21/00* (2013.01); *B23P 21/002* (2013.01); *G05B 2219/33007* (2013.01); *G05B 2219/35464* (2013.01); *G05B 2219/37297* (2013.01); *G05B 2219/39004* (2013.01); *G05B 2219/39102* (2013.01); *G05B 2219/39439* (2013.01); *G05B 2219/39531* (2013.01); *G05B 2219/39533* (2013.01); *G05B 2219/40022* (2013.01); *G05B 2219/40134* (2013.01); *G05B 2219/40136* (2013.01); *G05B 2219/40139* (2013.01); *G05B 2219/40142* (2013.01); *G05B 2219/40143* (2013.01); *G05B 2219/40145* (2013.01); *G05B 2219/40146* (2013.01); *G05B 2219/40161* (2013.01); *G05B 2219/40162* (2013.01); *G05B 2219/40163* (2013.01); *G05B 2219/40169* (2013.01); *G05B 2219/40182* (2013.01); *G05B 2219/40183* (2013.01); *G05B 2219/40195* (2013.01); *G05B 2219/40387* (2013.01); *G05B 2219/40627* (2013.01); *Y10S 901/02* (2013.01); *Y10S 901/03* (2013.01); *Y10S 901/08* (2013.01); *Y10S 901/09* (2013.01); *Y10S 901/10* (2013.01); *Y10S 901/27* (2013.01); *Y10S 901/41* (2013.01); *Y10S 901/46* (2013.01); *Y10S 901/47* (2013.01)

(58) Field of Classification Search
CPC ...... B25J 9/1646; B25J 9/1653; B25J 9/1674; B25J 9/1612; B25J 19/028; B25J 9/1602; B25J 13/085; B25J 13/087; B25J 9/0084; B25J 9/1697; B25J 13/006; B25J 13/08; B25J 3/00; B25J 9/1669; B25J 13/06; B25J 13/088; B25J 18/00; B25J 9/161; B25J 9/1664; B25J 9/1682; B25J 9/1689; B25J 19/023; B25J 3/04; B25J 9/1633; B25J 9/1628; B25J 13/02; B25J 9/163; B25J 11/008; B25J 13/003; B25J 13/065; B25J 13/025; B25J 13/084; B23Q 15/12; G06F 3/017

See application file for complete search history.

(56) References Cited

FOREIGN PATENT DOCUMENTS

| | | |
|---|---|---|
| JP | 2003-311661 A | 11/2003 |
| JP | 2010-131705 A | 6/2010 |
| JP | 2011-110620 A | 6/2011 |
| JP | 2014-104527 A | 6/2014 |
| WO | 2015/194658 A1 | 12/2015 |

OTHER PUBLICATIONS

JP09-216183 in view of JPO English Translation (Year: 2009).*
JPO English Translation: Masaki, JP 2011-110620 (Year: 2011).*
Aug. 9, 2016 Search Report issued in International Patent Application No. PCT/JP2016/002594.
Feb. 27, 2018 International Preliminary Report on Patentability issued in International Patent Application No. PCT/JP2016/002594.

* cited by examiner

| | FIRST HAND GESTURE | SECOND HAND GESTURE |
|---|---|---|
| HAND SHAPE HAND MOTION |  |  |
| INSTRUCTION TARGET | FIRST ROBOT MAIN BODY | SECOND ROBOT MAIN BODY |

FIG. 4

| | THIRD HAND GESTURE | FOURTH HAND GESTURE |
|---|---|---|
| HAND SHAPE HAND MOTION |  |  |
| INSTRUCTION CONTENT | CONTINUE WORK | SUSPEND WORK EXECUTION |

FIG. 5

|  | FIRST SOUND | SECOND SOUND |
| --- | --- | --- |
| SOUND CONTENT | "FIRST ROBOT" | "SECOND ROBOT" |
| INSTRUCTION TARGET | FIRST ROBOT MAIN BODY | SECOND ROBOT MAIN BODY |

FIG. 6

|  | THIRD SOUND | FOURTH SOUND |
| --- | --- | --- |
| SOUND CONTENT | "CONTINUE" | "WAIT" |
| INSTRUCTION CONTENT | CONTINUE WORK | SUSPEND WORK EXECUTION |

| | RIGHT-HAND OPERATION INSTRUCTING ACTION GROUP | | LEFT-HAND OPERATION INSTRUCTING ACTION GROUP | |
|---|---|---|---|---|
| HAND SHAPE HAND MOTION | FIFTH HAND GESTURE | SIXTH HAND GESTURE | SEVENTH HAND GESTURE | EIGHTH HAND GESTURE |
| INSTRUCTION TARGET | FIRST ROBOT MAIN BODY | FIRST ROBOT MAIN BODY | SECOND ROBOT MAIN BODY | SECOND ROBOT MAIN BODY |
| INSTRUCTION CONTENT | CONTINUE WORK | SUSPEND WORK EXECUTION | CONTINUE WORK | SUSPEND WORK EXECUTION |

FIG. 9

REMOTE CONTROL ROBOT SYSTEM

TECHNICAL FIELD

The present disclosure relates to a remote control robot system.

BACKGROUND ART

Conventionally, systems including a remote operation control device which causes a robot to perform a necessary work are known (e.g., see Patent Document 1).

This system includes a robot installed in a work environment and the remote operation control device which causes the robot to perform the necessary work while remotely controlling the robot by an operation control system. Thus, it is possible to remotely control the robot.

REFERENCE DOCUMENT OF CONVENTIONAL ART

Patent Document

[Patent Document 1] JP2003-311661A

DESCRIPTION OF THE DISCLOSURE

Problems to be Solved by the Disclosure

Meanwhile, for example, in order to improve productivity in a production system, it may be considered to sequentially perform in a given work place a plurality of processes by using a plurality of robots. In this case, there has been a problem that if the work processes are planned to avoid interference of the plurality of robots with each other in advance, it cannot flexibly respond to a change in production plan.

Therefore, in order to flexibly respond to the change in production plan, it may be considered to give an instruction to each robot according to the progression of the process so that the plurality of robots do not interfere each other, but there has been a problem that a configuration of a manipulating means of the robot becomes complex. Further, with the configuration of the manipulating means being complex, there has been a problem that a required education period for an operator to be familiar with the method of controlling the manipulating means becomes longer.

SUMMARY OF THE DISCLOSURE

In order to solve the above problems, a remote control robot system according to one aspect of the present disclosure includes a plurality of robot main bodies, a remote control device including a contactless action detecting part configured to detect a contactless action including at least one given operation instructing action by an operator, and a control device communicably connected to the remote control device and configured to control operations of the plurality of robot main bodies. The control device includes a memory part configured to store operational instruction content data defining an operation mode of the robot main body corresponding to the at least one operation instructing action, an operational instruction content identifying module configured to identify the operation mode of the robot main body corresponding to one of the operation instructing action detected by the contactless action detecting part based on the operational instruction content data, and a motion controlling module configured to control operation of at least one given robot main body among the plurality of robot main bodies based on the operation mode identified by the operational instruction content identifying module.

With this configuration, an action matching an operator's impression on the operational instruction content can be set as the operation instructing action, and a required education period for the operator to be familiar with the method of manipulating the remote control robot system can be shortened.

Further, since it is possible to input the operational instruction to the contactless action detecting part without touching, there is no need to visually recognize the contactless action detecting part at the time of inputting the operational instruction to the contactless action detecting part, and it is possible to promptly input the operational instruction to the contactless action detecting part.

Furthermore, it is possible that actions which are clearly distinguishable from each other as the respective operation instructing actions are selected and set as the operation instructing actions, preventing incorrect input and erroneous recognition by the operator.

The motion controlling module may control operations of all robot main bodies out of the plurality of robot main bodies based on the operation mode identified by the operational instruction content identifying module.

With this configuration, the operations of the plurality of robot main bodies can be controlled in a bulk. Note that the "all robot main bodies out of the plurality of robot main bodies" means all the robot main bodies.

The contactless action detected by the contactless action detecting part may further include at least one given instruction target specification instructing action of the operator. The memory part may further store instruction target specifying instruction data defining at least one robot main body among the plurality of robot main bodies which corresponds to the at least one instruction target specification instructing action, as an instruction target. The control device may further include an instruction target specifying module configured to specify as the instruction target the at least one given robot main body corresponding to one of the instruction target specification instructing action detected by the contactless action detecting part based on the instruction target specifying instruction data. The motion controlling module may control the operation of the at least one given robot main body specified by the instruction target specifying module out of the plurality of robot main bodies, based on the operation mode identified by the instruction content identifying module.

With this configuration, the operator is able to select as the instruction target, the at least one robot main body of which the operation is to be controlled out of the plurality of robot main bodies so as to control the robot main body related to the instruction target.

The operation instructing action may be operator's hand gesture.

With this configuration, the operator can input the operational instruction by his/her hand gesture.

The operation instructing action may be operator's sound of voice.

With this configuration, the operational instruction can be inputted to the remote control robot system by the operator's sound of voice.

The contactless action may include a plurality of operation instructing action groups, each comprised of at least one given operation instructing action in which the operator moves a body part, and the plurality of operation instructing action groups may be actions associated to a plurality of different body parts of the operator. The operational instruction content data may further define at least one given robot main body among the plurality of robot main bodies which corresponds to one of the plurality of operation instructing action groups, as an instruction target. The control device may further include an instruction target specifying module configured to specify as the instruction target the at least one given robot main body corresponding to the instruction target specification instructing action group to which one of the operation instructing action detected by the contactless action detecting part belongs, based on the operational instruction content data. The motion controlling module may control the operation of the at least one given robot main body specified by the instruction target specifying module out of the plurality of robot main bodies, based on the operation mode identified by the instruction content identifying module.

With this configuration, by moving a given body part, the operator is able to integrally input the instruction target specification instruction of the at least one robot main body of which the operation is to be controlled out of the plurality of robot main bodies and the operational instruction to the robot main body related to the instruction target. Thus, the instruction input can promptly be performed.

One operation instructing action group among the plurality of operation instructing action groups may include at least one given operation instructing action that is a hand gesture in which the operator moves a right hand, and another operation instructing action group among the plurality of operation instructing action groups may include at least one given operation instructing action that is a hand gesture in which the operator moves a left hand With this configuration, by moving the right and left hands, the operator is able to input the operational instructions to the robot main bodies each corresponding to one of the hands. Thus, the instruction input can promptly be performed.

The plurality of robot main bodies may respectively include a traveling unit configured to cause the robot main body to travel. The operation mode of the robot main body defined by the operational instruction content data may include an operation mode in which the robot main body travels by the traveling unit.

With this configuration, a traveling instruction for the traveling unit can be inputted to the remote control robot system by the operation instructing action.

Effect of the Disclosure

The present disclosure exerts an effect that the required education period for the operator to be familiar with the method of manipulating the remote control robot system can be shortened.

MODES FOR CARRYING OUT THE DISCLOSURE

Hereinafter, embodiments of the present disclosure will be described with reference to the accompanying drawings. Note that the present disclosure is not to be limited by these embodiments. Further, below, the same reference characters are assigned to the same or corresponding components throughout the figures and redundant description is omitted.

First Embodiment

Figure 1:
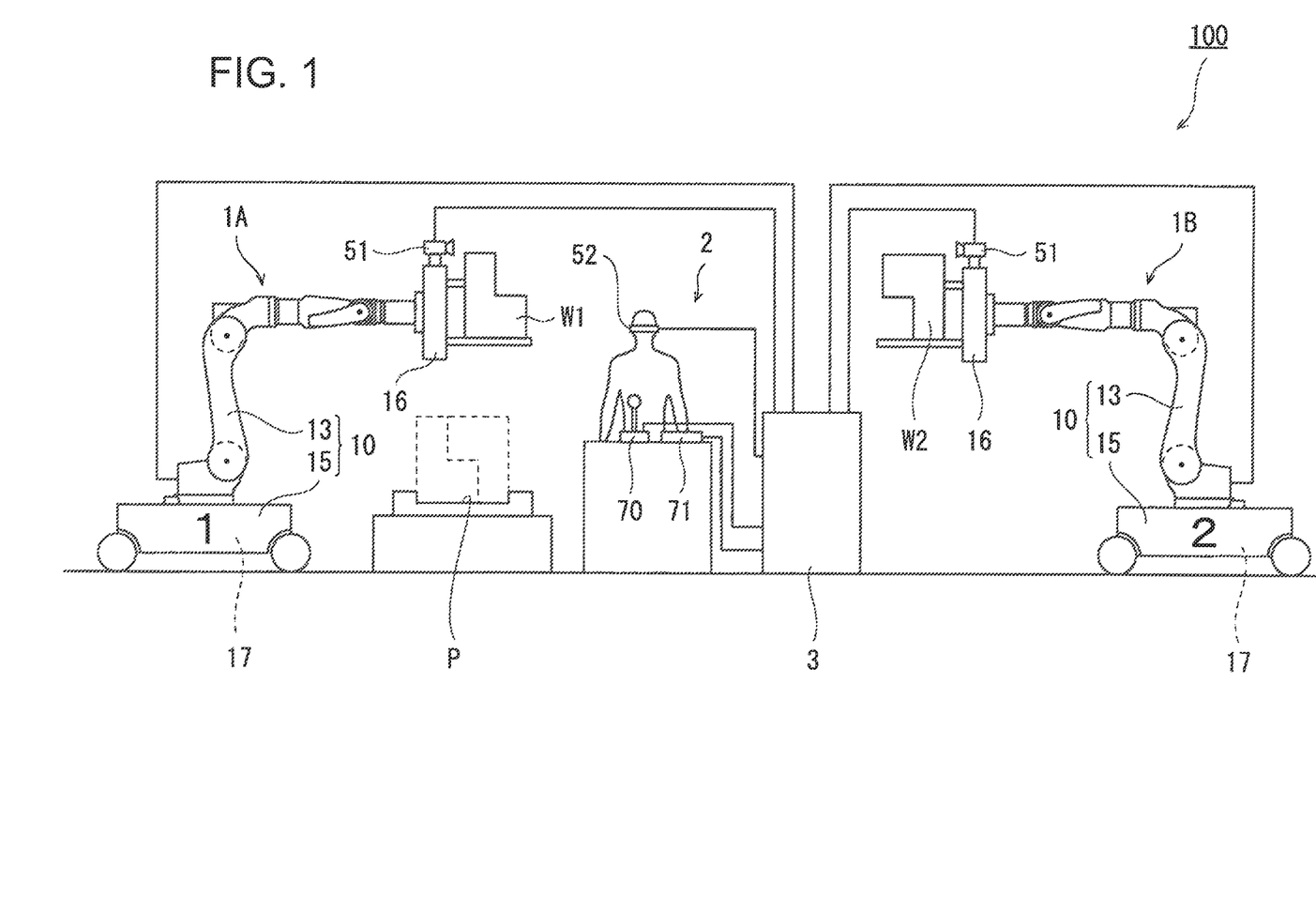
FIG. 1 is a view schematically illustrating a configuration example of a remote control robot system according to a first embodiment of the present disclosure.

FIG. 1 is a view schematically illustrating a configuration example of a remote control robot system 100 according to the first embodiment of the present disclosure.

As illustrated in FIG. 1, the remote control robot system 100 includes a plurality of robot main bodies 1, a remote control device 2, and a control device 3. In this embodiment, the remote control robot system 100 includes two robot main bodies 1 including a first robot main body 1A and a second robot main body 1B, but it may include three or more robot main bodies. Hereinafter, when particularly distinguishing the first robot main body 1A and the second robot main body 1B from each other, they are referred to as the first robot main body 1A and the second robot main body 1B, respectively, while not particularly distinguishing them, they are simply referred to as the robot main bodies 1.

The remote control robot system 100 according to this embodiment is a system including a master-slave type robot in which a slave arm operates following a motion of a master arm. The remote control robot system 100 is configured such that an operator located at a position distant from a working area of a slave arm 10 (details of the robotic arm will be described later) of the robot main body 1 (outside the working area) can input an operational instruction to the remote control robot system 100 by moving a master arm 70 of the remote control device 2 (details of a robotic arm operational instruction input part will be described later), to make the slave arm 10 perform an operation corresponding to the operational instruction by a control of the control device 3 to perform a specific work, such as an assembling work of components. The slave arm 10 of the remote control robot system 100 is also configured so that the slave arm 10 may automatically perform a given operation by a control of the control device 3 without the operator's control of the master arm 70.

[Configuration Example of Robot Main Body]

The robot main body 1 includes the slave arm 10, an end effector 16, a traveling unit 17, and a camera 51, and is installed in the working area.

The slave arm 10 is, for example, an arm of an articulated-type industrial robot, but it is not limited to this. The slave arm 10 includes an arm main body 13 and a pedestal 15.

The arm main body 13 includes a plurality of links sequentially connected in a direction from a base-end part toward a tip-end part, and one or more joints coupling the adjacent links so that one of them is rotatable with respect to the other link. Further, the end effector 16 is coupled to the tip-end part of the arm main body 13. Moreover, the arm main body 13 is configured so that the tip-end part is moved with respect to the base-end part by rotating the joint, and the end effector 16 thus moves within a given operational area. The arm main body 13 includes a robotic arm drive part (not illustrated) which drives a plurality of joint axes. Further, the pedestal 15 supports the arm main body 13 and the end effector 16.

In this embodiment, the end effector 16 is configured to be capable of performing a holding operation for holding a workpiece and a releasing operation for releasing the held workpiece, and is attached to the tip-end part of the arm main body 13 via a wrist joint. The end effector 16 includes an end effector drive part (not illustrated) for performing the holding operation and the releasing operation. In this embodiment, although the end effector 16 is configured to be capable of performing the holding operation and the releasing operation so that, for example, the assembling work of the components can be performed, it is not limited to this. Alternatively to this, it may be configured so that, for example, a welding work and a paint work can be performed.

The traveling unit 17 is provided to the pedestal 15 and causes the entire robot main body 1 to travel. The traveling unit 17 has, for example, wheels and a wheel drive part (not illustrated) which rotatably drives the wheels. The wheel drive part rotatably drives the wheels to move the robot main body 1. Thus, in this embodiment, the robot main body 1 is a self-running robot which is self-runnable, but it is not limited to this.

The camera 51 is a camera which images operation statuses of the slave arm 10 and the end effector 16. In this embodiment, the camera 51 is attached to the end effector 16, but it is not limited to this. Alternatively to this, it may be attached to the tip end part of the slave arm 10 or the pedestal 15. Further, it may be fixed at a given position in the working area.

[Configuration Example of Remote Control Device]

The remote control device 2 is installed outside the working area, is communicably connected to the control device 3, and controls the operation of the robot main body 1.

The remote control device 2 includes the master arm 70, a contactless action detecting part 71, and a monitor 52.

The master arm 70 is a device for the operator to input an operational instruction for the slave arm 10 from the operator. In this embodiment, the master arm 70 is a device which the operator can control by touching, to input a target attitude of the slave arm 10 and input an operation mode for the slave arm 10.

Figure 2:
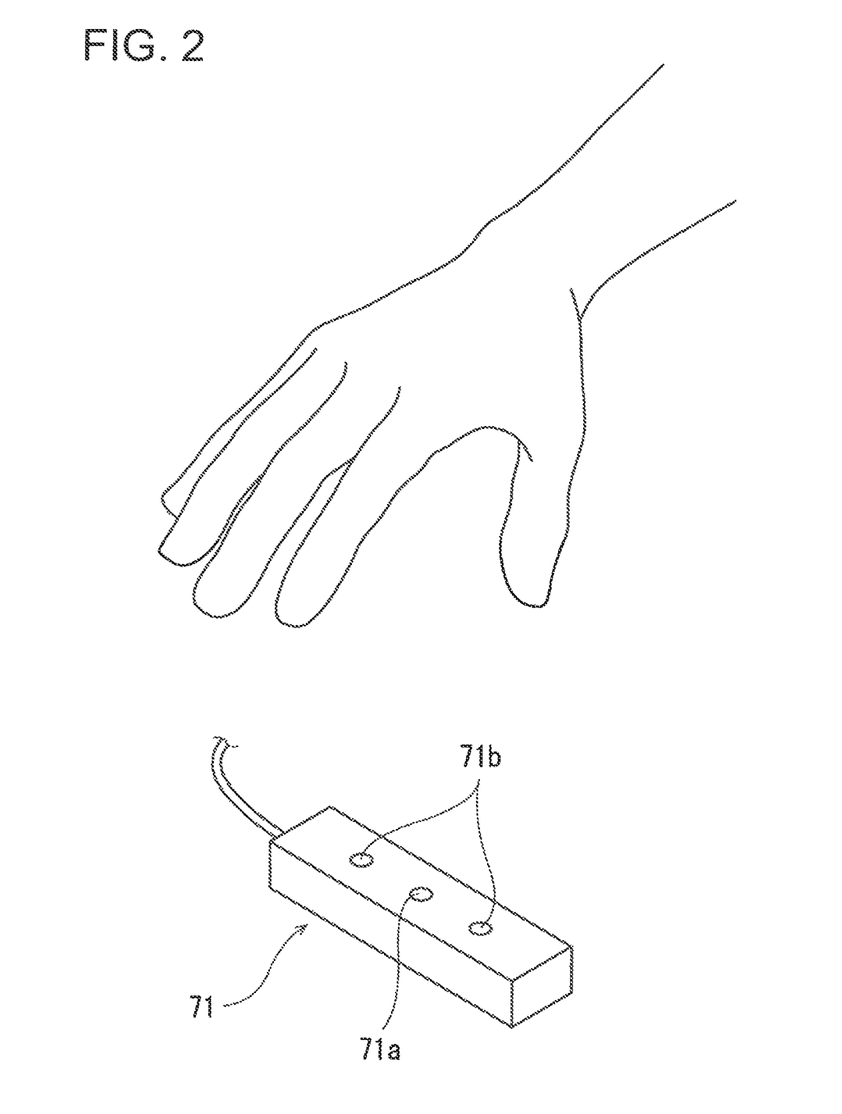
FIG. 2 is a perspective view illustrating a configuration example of a contactless action detecting part of the remote control robot system in FIG. 1.

FIG. 2 is a perspective view illustrating a configuration example of the contactless action detecting part 71.

The contactless action detecting part 71 detects a contactless action which includes operator's one or more given instruction target specification instructing actions and one or more given operation instructing actions within a given detection range. The contactless action refers to actions related to body gestures, hand gestures, and vocalizations of the operator, and does not include actions of touching an input device to control it. The contactless action includes, for example, the operator making a hand gesture, the operator speaking, the operator exhaling, the operator changing his/her posture, the operator shaking his/her neck up-and-down or to the sides, the operator tilting the neck, the operator blinking, the operator gazing at a given place, the operator changing his/her facial expression, the operator stomping, and the operator chewing.

In this embodiment, the given instruction target specification instructing action and the given operation instructing action are to cause the operator to make the hand gesture, and the contactless action detecting part 71 is a detector which detects the operator's hand gesture within a range set above the contactless action detecting part 71. As illustrated in FIG. 2, the contactless action detecting part 71 includes an infrared radiator 71a for radiating an infrared ray upwardly and a stereo camera 71b for receiving the infrared ray radiated from the infrared radiator 71a and reflected on a target object. It is further configured to calculate an attitude of each finger (a shape of a hand) and a motion of the hand based on an image captured by the stereo camera 71b. Further, the contactless action detecting part 71 is installed near the master arm 70 and configured to be capable of manipulating the robot main body 1 while parallelly performing an input of the operational instruction to the master arm 70 and an input of the instruction to the contactless action detecting part 71. For example, LEAP (®) of Leap Motion Inc. may be used as the contactless action detecting part 71.

The monitor 52 is a monitor for the operator to confirm a work situation of the slave arm 10. The monitor 52 is installed in a space where the master arm 70 is provided. Further, in this embodiment, the monitor 52 is, for example, a head mounted display which may be attached to the operator's head, but it is not limited to this.

[Configuration Example of Control Device]

Figure 3:
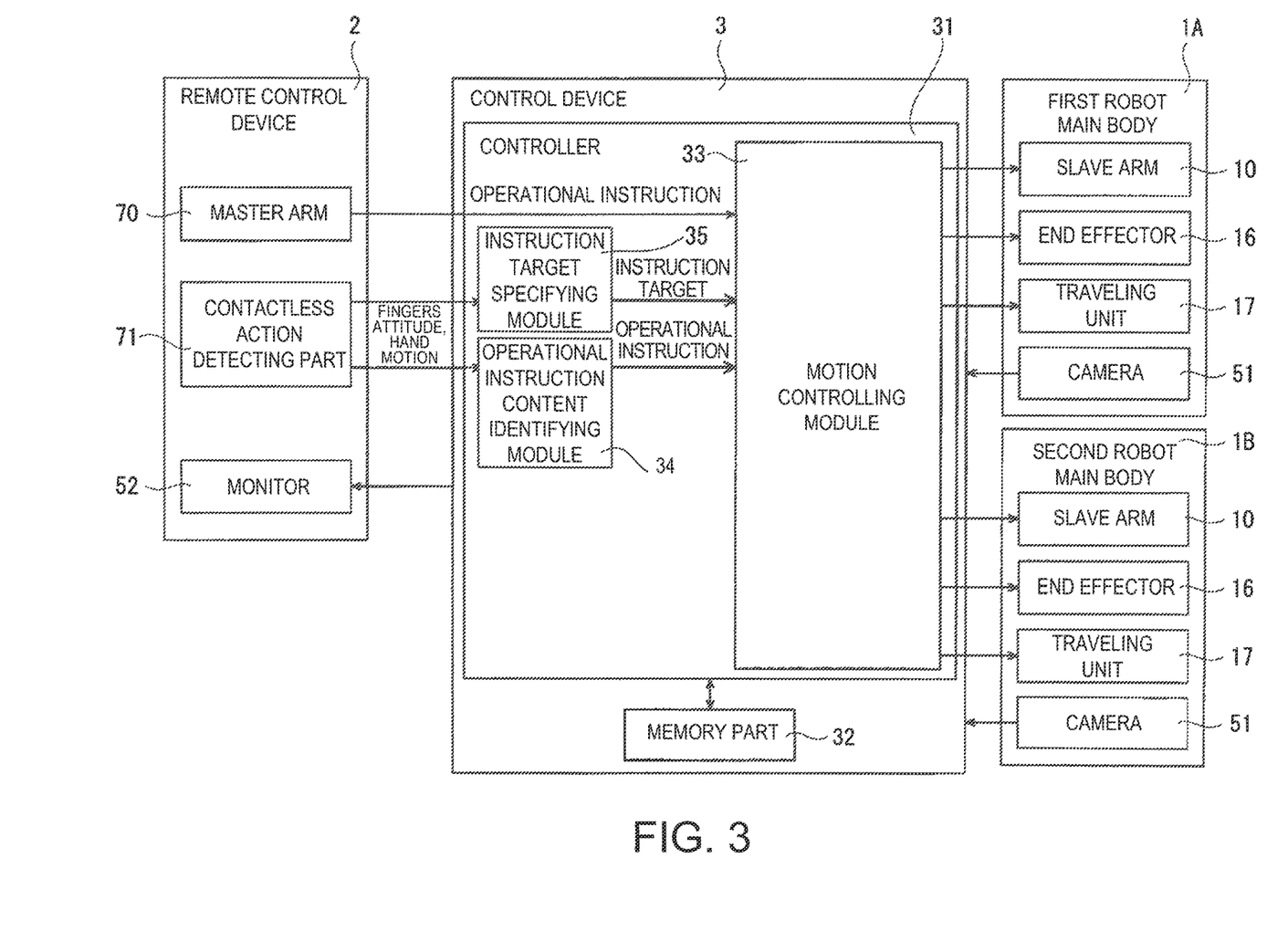
FIG. 3 is a block diagram schematically illustrating a configuration example of a control system of the remote control robot system in FIG. 1.

FIG. 3 is a block diagram schematically illustrating a configuration example of a control system of the remote control robot system 100.

The control device 3 is communicably connected to the remote control device 2 and controls the operations of the first robot main body 1A and the second robot main body 1B.

As illustrated in FIG. 3, the control device 3 includes a controller 31 and a memory part 32. The control device 3 may be comprised of a single controller which performs a central control or a plurality of controllers which perform distributed controls.

The controller 31 is, for example, comprised of a microcontroller, a CPU, an MPU, a logic circuit, a PLC, etc.

The controller 31 includes a motion controlling module 33, an instruction target specifying module 35, and an operational instruction content identifying module 34. The motion controlling module 33, the instruction target specifying module 35, and the operational instruction content identifying module 34 are functional blocks implemented by an arithmetic unit executing a given control program stored in the memory part 32.

The motion controlling module 33 controls the operation of the robot main body 1, including the operation of the slave arm 10, the operation of the end effector 16, and the operation of the traveling unit 17. The controls of the operation of the end effector 16 and the operation of the traveling unit 17 are performed, for example, by controlling a current supplied to each drive part.

The motion controlling module 33 manipulates the slave arm 10 based on the operational instruction inputted to the master arm 70, and further controls the operation of one or more given robot main bodies 1 (instruction target) among the plurality of robot main bodies 1 based on an operation mode identified by the operational instruction content identifying module 34. In this embodiment, when the contactless action detecting part 71 detects an operation instructing action within a given time after the contactless action detecting part 71 detects the instruction target specification instructing action, the motion controlling module 33 controls the operation of one of the first robot main body 1A and the second robot main body 1B specified by the instruction target specifying module 35 described later. On the other hand, when the contactless action detecting part 71 does not detect the instruction target specification instructing action but only detects the operation instructing action, the motion controlling module 33 controls the operations of the first robot main body 1A and the second robot main body 1B.

Based on instruction target specifying data stored in the memory part 32, the instruction target specifying module 35 specifies as an instruction target at least one of the first robot main body 1A and the second robot main body 1B corresponding to a single hand gesture (instruction target specification instructing action) detected by the contactless action detecting part 71.

The operational instruction content identifying module 34, based on the operational instruction content data stored in the memory part 32, identifies the operation mode of the robot main body 1 corresponding to a single hand gesture (operation instructing action) detected by the contactless action detecting part 71.

In addition, the controller 31 is configured to process information of an image captured by the camera 51 and then output it to the monitor 52. Thus, the operator can control the master arm 70 while checking the work situation of the slave arm 10 displayed on the monitor 52. Note that the camera 51 and the monitor 52 may be connected directly to each other without going through the control device 3.

Figure 4:
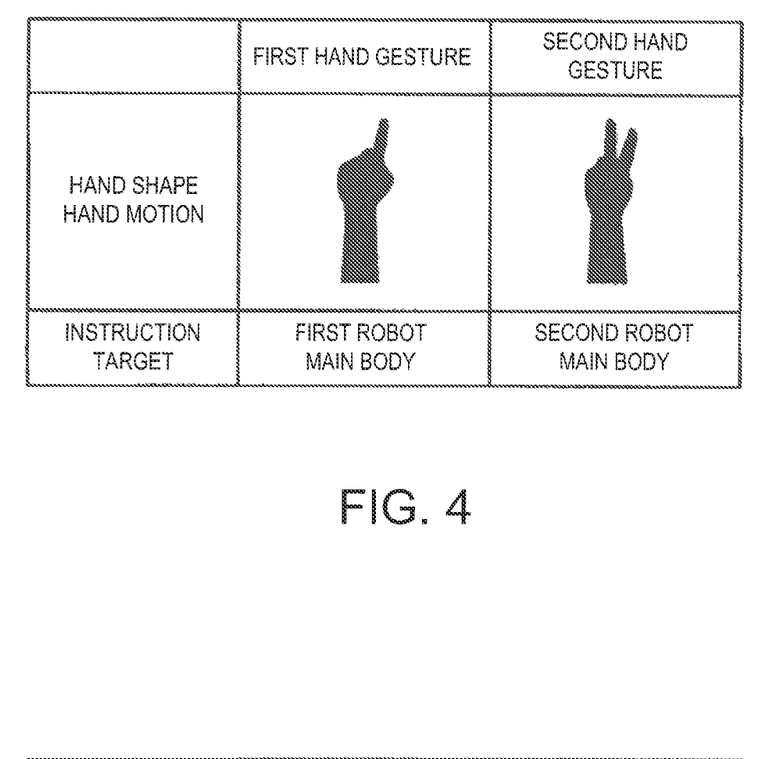
FIG. 4 is a view illustrating a configuration example of instruction target specifying data stored in a memory part of the remote control robot system in FIG. 1.
Figure 5:
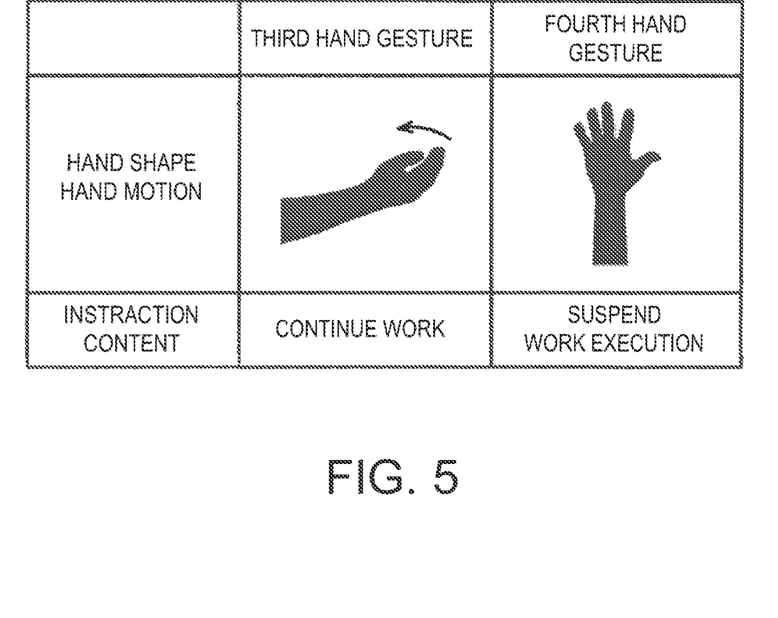
FIG. 5 is a view illustrating a configuration example of operational instruction content data stored in a memory part of the remote control robot system in FIG. 1.

FIG. 4 is a view illustrating a configuration example of the instruction target specifying data stored in the memory part 32. FIG. 5 is a view illustrating a configuration example of the operational instruction content data stored in the memory part 32.

The memory part 32 has memories, such as a ROM and a RAM. The memory part 32 stores given programs and the controller 31 reads and executes these control programs to control the operation of the robot main body 1.

Further, as illustrated in FIG. 4, the memory part 32 stores instruction target specifying data which defines as the instruction target one of the first robot main body 1A and the second robot main body 1B corresponding to the one or more instruction target specification instructing actions (hand gestures).

That is, in this embodiment, the instruction target specifying instruction data includes a definition in which the first robot main body 1A becomes the instruction target in association with a first hand gesture in which the index finger is stretched and the other fingers are bent, and a definition in which the second robot main body 1B becomes the instruction target in association with a second hand gesture in which the index finger and the middle finger are stretched and the other fingers are bent.

Further, as illustrated in FIG. 5, the memory part 32 stores operational instruction content data defining the operation mode of the robot main body 1 corresponding to the one or more operation instructing actions (hand gestures).

That is, in this embodiment, the operational instruction content data includes definitions of operation modes related to "continue work" and "suspend work execution" which are associated with given hand gestures.

First, a third hand gesture in which finger tips other than the thumb are bent and stretched with the palm facing up is associated with the operation mode related to "continue work." The operation mode related to "continue work" is a mode in which the robot main body 1 is caused to continue the work in execution or continue the execution of the work suspended from execution.

Further, as illustrated in FIG. 4, a fourth hand gesture in which fingers are stretched with the palm facing forward is associated with the operation mode related to "suspend work execution." The operation mode related to "suspend work execution" is a mode in which the work in execution is temporarily suspended.

The first to fourth hand gestures are not limited to the modes described above but hand gestures matching an operator's impression on the instruction target and the operational instruction content may be selected and set as an instruction target specification instructing action and an operation instructing action. Thus, a required period of time for the operator to memorize the correspondence of the instruction target specifying instruction and the operational instruction with the hand gesture (operation instructing action) and be familiar with the method of manipulating the remote control robot system 100 can be shortened.

Further, since it is possible to input the instruction target specifying instruction and the operational instruction to the contactless action detecting part 71 without touching, there is no need to visually recognize the contactless action detecting part 71 at the time of the input operation of the instruction target specifying instruction and the operational instruction to the contactless action detecting part 71, and it is possible to, for example, input the instruction target specifying instruction and the operational instruction to the contactless action detecting part 71 while keeping the focus on the monitor 52. Therefore, it is possible to promptly input the instruction target specifying instruction and the operational instruction, and it is possible to prevent the work from being interrupted by moving his/her eyes away from the monitor 52.

Furthermore, it is possible that hand gestures which are clearly distinguishable as the respective hand gestures from each other are selected and set as the instruction target specification instructing actions and the operation instructing actions, preventing incorrect input and erroneous recognition by the operator.

Note that in this embodiment, the first to fourth hand gestures are all inputted by one of the operator's hands. Thus, it is possible to make hand gestures to input the instruction target specifying instruction and the operational instruction to the remote control robot system 100 with one hand, while simultaneously controlling the master arm 70 to input the operational instruction for the slave arm 10 to the remote control robot system 100 with the other hand. As a result, a plurality of operational instruction inputs are possible.

The signals outputted from the master arm 70 and the contactless action detecting part 71 of the remote control device 2 are inputted to the control device 3. Further, the signal outputted from the camera 51 is inputted to the control device 3.

It is configured such that the communication between the remote control device 2 and the control device 3 and the communication between the control device 3 and the robot main body 1 are performed by a manner of using wire or wirelessly as appropriate.

[Operation Example]

Next, an operation example of the remote control robot system 100 will be described.

This operation example is an operation example in a case where a workpiece W1 stored in a workpiece storage is installed at an installation position P (see FIG. 1), and then a workpiece W2 stored in the workpiece storage is installed at the installation position P.

First, while the first robot main body 1A and the second robot main body 1B are traveling toward the installation position P, when the operator makes the fourth hand gesture which includes the hand shape indicating a standby in order to stop the first robot main body 1A and the second robot main body 1B once, the contactless action detecting part 71 detects the fourth hand gesture and transmits the attitudes of the respective fingers and the hand motion related to the fourth hand gesture to the control device 3. Then, the operational instruction content identifying module 34 determines that the operational instruction related to the operation mode of "suspend work execution" has been inputted to the remote control robot system 100 based on the fourth hand gesture. Then, the motion controlling module 33 controls the traveling units 17 of the first robot main body 1A and the second robot main body 1B to suspend (stop) the first robot main body 1A and the second robot main body 1B from advancing.

Next, when the operator makes the third hand gesture which includes the hand shape and motion like beckoning in order to cause the first robot main body 1A and the second robot main body 1B to travel toward the installation position P, the operational instruction content identifying module 34 determines that the operational instruction related to the operation mode of "continue work" has been inputted to the remote control robot system 100 based on the third hand gesture. Then, the motion controlling module 33 controls the traveling units 17 of the first robot main body 1A and the second robot main body 1B to cause the first robot main body 1A and the second robot main body 1B to advance and travel toward the installation position P.

Next, in a state where the first robot main body 1A arrives near the installation position P first and the operator controls the master arm 70 to manipulate the slave arm 10 and move the workpiece W held by the end effector 16 toward the installation position P, when the second robot main body 1B approaches the installation position P, the operator causes the second robot main body 1B to standby until the installation of the workpiece W1 to the installation position P by the first robot main body 1A completes.

That is, when the operator makes the second hand gesture having the hand shape indicating "2," the instruction target specifying module 35 specifies the second robot main body 1B as the instruction target based on the second hand gesture.

Subsequently to the second hand gesture, when the operator makes the fourth hand gesture which includes the hand shape indicating the standby, the operational instruction content identifying module 34 determines that the operational instruction related to the operation mode of "suspend work execution" has been inputted to the remote control robot system 100 based on the fourth hand gesture. Then, the motion controlling module 33 controls the traveling unit 17 of the second robot main body 1B to suspend (stop) the second robot main body 1B from advancing.

When the installation of the workpiece W1 at the installation position P by the first robot main body 1A is completed and the installation of the workpiece W2 at the installation position P by the second robot main body 1B becomes possible, the operator makes the second hand gesture, followed by the third hand gesture. Thus, the instruction target specifying module 35 specifies the second robot main body 1B as the instruction target based on the second hand gesture, and further the operational instruction content identifying module 34 determines that the operational instruction related to the operation mode of "continue work" has been inputted to the remote control robot system 100 based on the third hand gesture. Then, the motion controlling module 33 controls the traveling unit 17 of the second robot main body 1B to cause the second robot main body 1B to advance and install the workpiece W at the installation position P. Thus, the second robot main body 1B can be promptly moved toward the installation position P after the first robot main body 1A installs the workpiece W1 at the installation position P, thus improving work efficiency.

As described above, in the remote control robot system 100 according to the present disclosure, the operator can select and set the actions matching the impression on the operational instruction content as the instruction target specification instructing action and the operation instructing action and, by using the set instruction target specification instructing action and operation instructing action, input to the remote control robot system 100 the operational instruction corresponding to the operation instructing action for the instruction target corresponding to the instruction target specification instructing action. Thus, a required period of time for the operator to memorize the correspondence between the instruction target and the hand gesture (instruction target specification instructing action) and the correspondence between the operational instruction and the hand gesture (operation instructing action) and be familiar with the method of manipulating the remote control robot system 100 can be shortened.

Further, since it is possible to input the instruction target specifying instruction and the operational instruction to the contactless action detecting part 71 without touching, there is no need to visually recognize the contactless action detecting part 71 at the time of the input operation of the instruction target specifying instruction and the operational instruction to the contactless action detecting part 71, and it is possible to, for example, input the instruction target specifying instruction and the operational instruction to the contactless action detecting part 71 while keeping the focus on the monitor 52. Therefore, it is possible to promptly input the instruction target specifying instruction and the operational instruction, and it is possible to prevent the work from being interrupted by moving his/her eyes away from the monitor 52.

Furthermore, it is possible that actions which are clearly distinguishable from each other as the respective instruction target specification instructing action and operation instructing action are selected and set as the instruction target specification instructing action and operation instructing action, preventing incorrect input and erroneous recognition by the operator.

Second Embodiment

Hereinafter, configurations and operations of the second embodiment will be described focusing on differences from the first embodiment.

Figure 6:
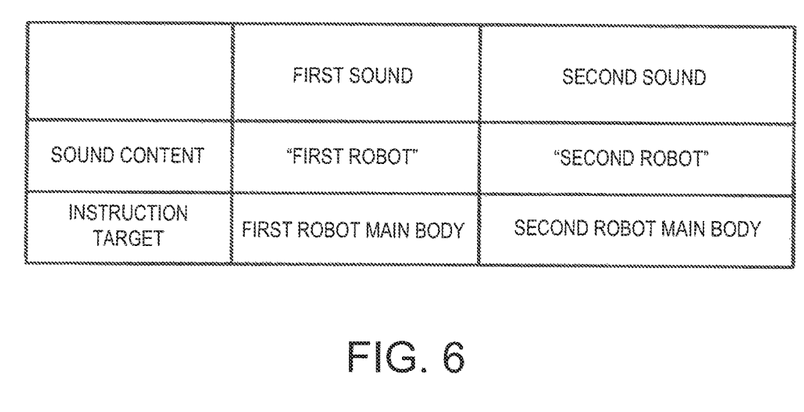
FIG. 6 is a view illustrating a configuration example of instruction target specifying data according to a second embodiment of the present disclosure.
Figure 7:
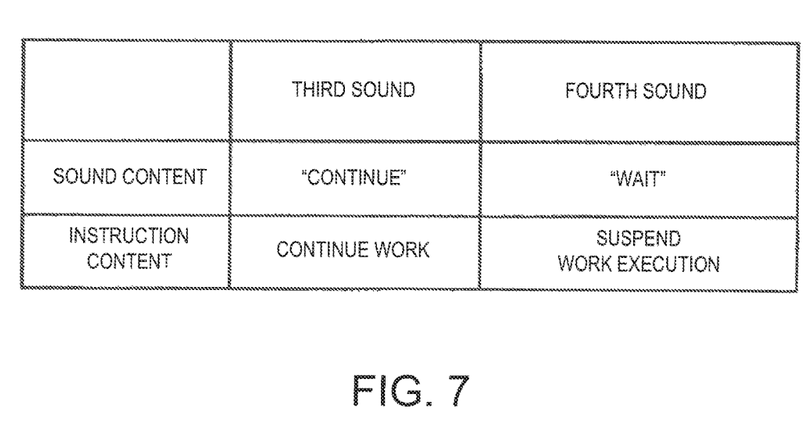
FIG. 7 is a view illustrating a configuration example of operational instruction content data according to the second embodiment of the present disclosure.

FIG. 6 is a view illustrating a configuration example of instruction target specifying data according to this embodiment, which is stored in the memory part 32. FIG. 7 is a view illustrating a configuration example of operational instruction content data according to this embodiment, which is stored in the memory part 32.

In the first embodiment, the instruction target specification instructing action and the operation instructing action are the operator's hand gestures, and the contactless action detecting part 71 is the detector for detecting the operator's hand gestures. Meanwhile in this embodiment, the instruction target specification instructing action and the operation instructing action are operator's sound of voice, and the contactless action detecting part is a detector for detecting the sound, for example, a microphone.

Further, in the first embodiment, the memory part 32 stores the instruction target specifying data which defines one of the first robot main body 1A and the second robot main body 1B which is associated with a given hand gesture as the instruction target, and the operational instruction content data which contains the definition of the operational instructions related to "continue work" and "suspend work execution" which are associated with given hand gestures. Meanwhile in this embodiment, the memory part 32 stores instruction target specifying data which defines one of the first robot main body 1A and the second robot main body 1B which is associated with a given sound as the instruction target, and operational instruction content data which contains a definition of the operational instruction related to "continue work" and "suspend work execution" which are associated with given sounds.

As illustrated in FIG. 6, the instruction target specifying data includes a definition in which the first robot main body 1A becomes the instruction target in association with a first sound related to a sound of voice "first robot" and a definition in which the second robot main body 1B becomes the instruction target in association with a second sound related to a sound of voice "second robot." Further, as illustrated in FIG. 7, the operational instruction content data includes a definition of the operation mode related to "continue work" which is associated with a third sound related to a sound of voice "continue," and a definition of the operation mode related to "suspend work execution" which is associated with a fourth sound related to a sound of voice "wait." Note that, the operation modes related to "continue work" and "suspend work execution" are similar to those in the first embodiment.

As described above, in this embodiment, by inputting the first or second sound to the contactless action detecting part 71 followed by an input of the third or fourth sound, the motion controlling module 33 manipulates the instruction target corresponding to the first or second sound according to the operation mode corresponding to the third or fourth sound.

Third Embodiment

In the first embodiment, the contactless action detecting part 71 for detecting the operator's hand gesture includes the infrared radiator 71a, and the stereo camera 71b for receiving the infrared ray radiated from the infrared radiator 71a and reflected on the target object. Meanwhile in this embodiment, the contactless action detecting part 71 for detecting the operator's hand gesture is a glove to be worn on the operator's hand, and includes a sensor for detecting the attitude of each finger and the motion of the hand Fourth Embodiment Hereinafter, configurations and operations of a fourth embodiment will be described focusing on differences from the first embodiment.

Figure 8:
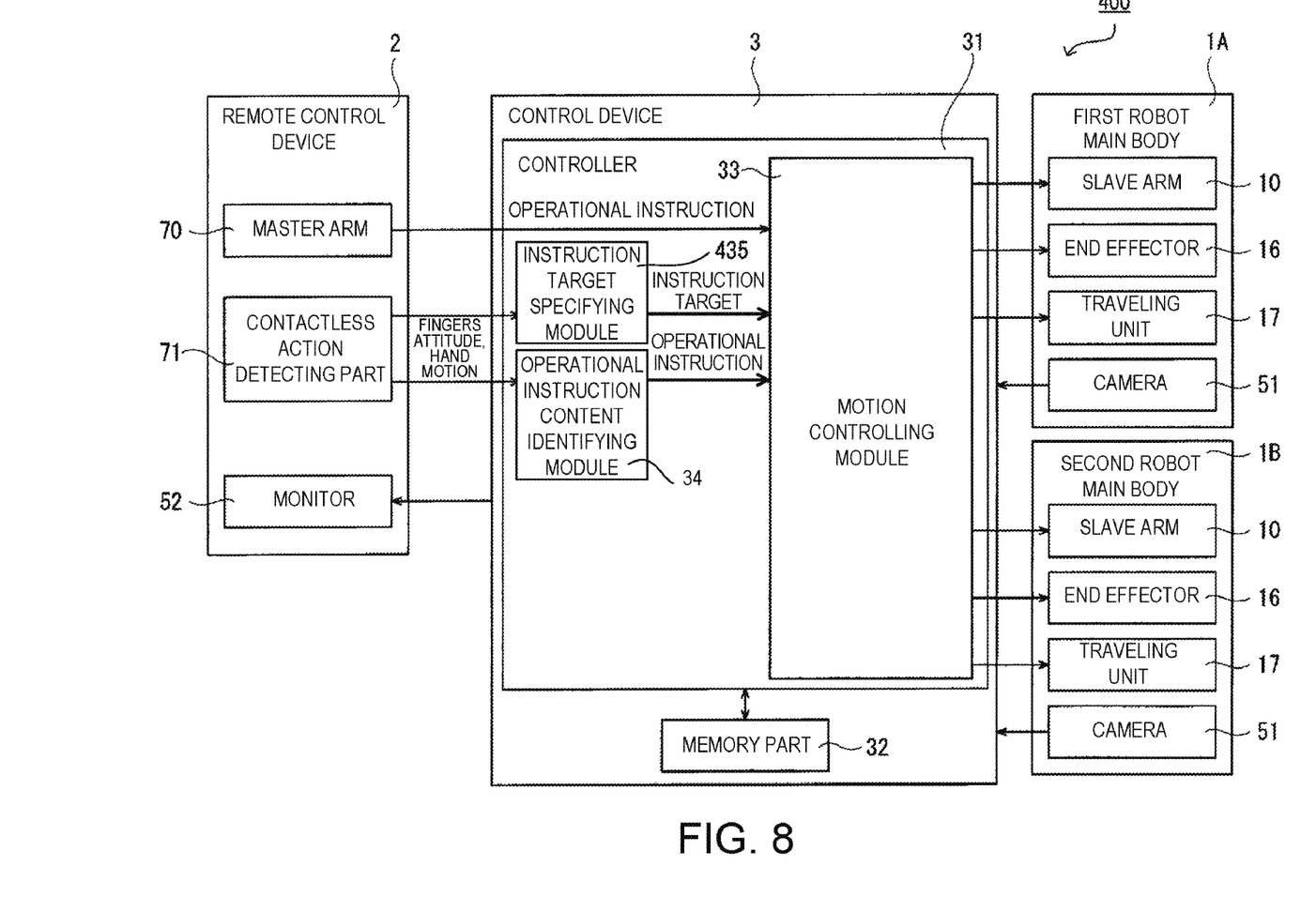
FIG. 8 is a block diagram schematically illustrating a configuration example of a control system of a remote control robot system according to a fourth embodiment of the present disclosure.

FIG. 8 is a block diagram schematically illustrating a configuration example of a control system of a remote control robot system according to this embodiment.

In this embodiment, the contactless action includes a plurality of operation instructing action groups, each comprised of one or more given operation instructing actions in which the operator moves his/her body part. Further, the plurality of operation instructing action groups are actions associated to a plurality of different body parts of the operator. Thus, the operation instructing actions which belong to different operation instructing action groups are associated to different body parts of the operator. On the other hand, one or more operation instructing actions which belong to the same operation instructing action group are associated to the same body part of the operator. For example, the contactless action includes a right-hand operation instructing action group in which a right hand is moved and a left-hand operation instructing action group in which a left hand is moved. Note that, alternatively to this, it may be a right-leg operation instructing action group in which a right left is moved and a left-leg operation instructing action group in which a left leg is moved.

Further, as illustrated in FIG. 8, based on the instruction target specifying data stored in the memory part 32, an instruction target specifying module 435 specifies as the instruction target one or more given robot main bodies corresponding to the operation instructing action group to which a single operation instructing action detected by the contactless action detecting part 71 belongs. For example, when an operation instructing action which belongs to the right-hand operation instructing action group is inputted to the contactless action detecting part 71, the instruction target specifying module 435 specifies the first robot main body 1A as the instruction target. On the other hand, when an operation instructing action which belongs to the left-hand operation instructing action group is inputted to the contactless action detecting part 71, the instruction target specifying module 435 specifies the second robot main body 1B as the instruction target.

Figure 9:
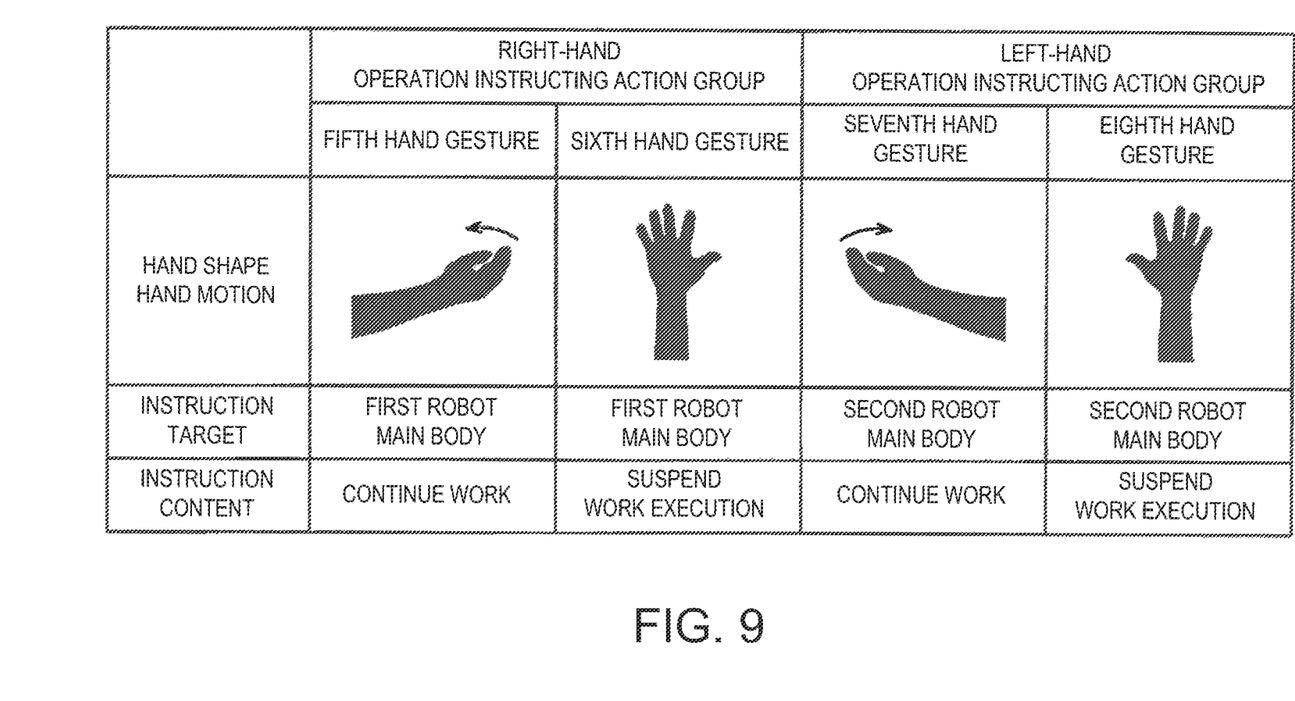
FIG. 9 is a view illustrating a configuration example of operational instruction content data stored in a memory part of the remote control robot system in FIG. 8.

FIG. 9 is a view illustrating a configuration example of operational instruction content data stored in a memory part of the remote control robot system.

Further, as illustrated in FIG. 9, the operational instruction content data stored in the memory part 32, similar to the first embodiment, defines the operational instruction for the robot main body 1 corresponding to one or more operation instructing actions (hand gestures) and, additionally, defines one or more given robot main bodies out of the plurality of robot main bodies 1 which corresponds to a plurality of operation instructing action groups, as the instruction target.

For example, the operational instruction content data includes the following definitions associated with given hand gestures. That is, a fifth hand gesture in which the right hand palm faces up and finger tips other than the thumb are bent and stretched belongs to the right-hand operation instructing action group, and this hand gesture is associated with the operation mode having the first robot main body as the instruction target and related to "continue work." The operation mode related to "continue work" is an instruction which includes an operational instruction similar to "continue work" in the first embodiment.

Further, a sixth hand gesture in which the right hand palm faces forward and fingers are stretched belongs to the right-hand operation instructing action group, and this hand gesture is associated with the operation mode having the first robot main body 1A as the instruction target and related to "suspend work execution." The operation mode related to "suspend work execution" is an instruction which includes an operational instruction similar to "suspend work execution" in the first embodiment.

Furthermore, a seventh hand gesture in which the left hand palm faces up and finger tips other than the thumb are bent and stretched belongs to the left-hand operation instructing action group, and this hand gesture is associated with the operation mode having the second robot main body 1B as the instruction target and related to "continue work."

Further, an eighth hand gesture in which the left hand palm faces forward and fingers are stretched belongs to the left-hand operation instructing action group, and this hand gesture is associated with the operation mode having the second robot main body 1B as the instruction target and related to "suspend work execution."

Thus, the right-hand operation instructing action group is assigned with the fifth and sixth hand gestures and has the first robot main body 1A as the instruction target. Further, the left-hand operation instructing action group is assigned with the seventh and eighth hand gestures and has the second robot main body 1B as the instruction target.

Furthermore, the fifth hand gesture and the seventh hand gesture which are mutual in terms of the finger tips other than the thumb being bent and stretched with the palm facing up are both associated with the operation modes related to "continue work."

Further, the sixth hand gesture and the eighth hand gesture which are mutual in terms of the fingers being stretched with the palm facing forward are both associated with the operation modes related to "suspend work execution."

Thus, in a remote control robot system 400, when the operator makes the fifth hand gesture, the instruction target specifying module 435 specifies the first robot main body 1A as the instruction target based on the fifth hand gesture, and further the operational instruction content identifying module 34 determines that the operational instruction related to the operation mode of "continue work" has been inputted to the remote control robot system 400 based on the fifth hand gesture. Then, the motion controlling module 33 controls the first robot main body 1A to continue the work in execution or continue the execution of the work suspended from execution.

Further, when the operator makes the sixth hand gesture, the instruction target specifying module 435 specifies the first robot main body 1A as the instruction target based on the sixth hand gesture, and further the operational instruction content identifying module 34 determines that the operational instruction related to the operation mode of "suspend work execution" has been inputted to the remote control robot system 400 based on the sixth hand gesture. Then, the motion controlling module 33 controls the first robot main body 1A to temporarily suspend the work in execution.

Further, when the operator makes the seventh hand gesture, the instruction target specifying module 435 specifies the second robot main body 1B as the instruction target based on the seventh hand gesture, and further the operational instruction content identifying module 34 determines that the operational instruction related to the operation mode of "continue work" has been inputted to the remote control robot system 400 based on the seventh hand gesture. Then, the motion controlling module 33 controls the second robot main body 1B to continue the work in execution or continue the execution of the work suspended from execution.

Further, when the operator makes the eighth hand gesture, the instruction target specifying module 435 specifies the second robot main body 1B as the instruction target based on the eighth hand gesture, and further the operational instruction content identifying module 34 determines that the operational instruction related to the operation mode of "suspend work execution" has been inputted to the remote control robot system 400 based on the eighth hand gesture. Then, the motion controlling module 33 controls the second robot main body 1B to temporarily suspend the work in execution.

Thus, by moving the right hand or the left hand, the operator can integrally input the instruction target specifying instruction for the robot main body 1 which is one of the first robot main body 1A and the second robot main body 1B of which the operation is to be controlled, and the operational instruction for the robot main body 1 related to the instruction target. Thus, the instruction can be inputted promptly.

<Modifications>

In the above embodiments, the master arm 70 is a device by which the target attitude of the slave arm 10 can be inputted, but it is not limited to this. Alternatively to this, the master arm may be a device by which a target position and target attitude of the end effector 16 are inputted. Further, the motion controlling module 33 may calculate the attitude of the slave arm 10 at which the end effecter takes the detected target position and target attitude, and control the operation of the slave arm 10 so that the slave arm 10 takes the attitude.

From the above description, many improvements and other embodiments of the present disclosure are apparent for a person skilled in the art. Therefore, the above description is to be interpreted only as illustration, and it is provided in order to teach a person skilled in the art the best mode in which the present disclosure is implemented. Details of the structures and/or functions of the present disclosure may be substantially changed without departing from the spirit of the present disclosure.

DESCRIPTION OF REFERENCE CHARACTERS

1A First Robot Main Body
1B Second Robot Main Body
2 Remote Control Device
3 Control Device
10 Slave Arm
13 Arm Main Body
15 Pedestal
16 End Effector
17 Traveling Unit
31 Controller
32 Memory Part
33 Motion Controlling Module
34 Operational Instruction Content Identifying Module
35 Instruction Target Specifying Module
51 Camera
50 Monitor
70 Master Arm
71 Contactless Action Detecting Part
100 Remote Control Robot System

The invention claimed is:

1. A remote control robot system, comprising:
a plurality of robot main bodies;
a remote control device including a contactless action detecting part configured to detect a contactless action including at least one given operation instructing action by an operator and at least one given instruction target specification instructing action by the operator, the at least one given instruction target specification instructing action being distinguishable from the at least one given operation instructing action; and a control device communicably connected to the remote control device and configured to control operations of the plurality of robot main bodies, the control device including:

a memory configured to store operational instruction content data defining at least one operation mode of the robot main bodies which corresponds to the at least one operation instructing action and further store instruction target specifying data defining at least one given robot main body among the robot main bodies which corresponds to the at least one instruction target specification instructing action, as an instruction target; and a processor programed to:

when the contactless action detecting part detects the instruction target specification instructing action, specify the at least one given robot main body corresponding to the detected instruction target specification instructing action as the instruction target based on the instruction target specifying instruction data;

when the contactless action detecting part detects the operation instructing action but does not detect the instruction target specification instructing action, specify the plurality of robot main bodies as the instruction target;

identify the operation mode corresponding to the detected operation instructing action based on the operational instruction content data; and control the operation of the instruction target based on the identified operation mode.

2. The remote control robot system of claim 1, wherein the operation instructing action is a hand gesture of the operator.

3. The remote control robot system of claim 1, wherein the operation instructing action is a sound of voice of the operator.

4. The remote control robot system of claim 1, wherein each of the plurality of robot main bodies includes a traveling unit configured to cause the robot main body to travel, and wherein the at least one operation mode defined by the operational instruction content data includes an operation mode in which the robot main body travels by the traveling unit.

* * * * *